(12) United States Patent
Moon et al.

(10) Patent No.: US 12,252,523 B2
(45) Date of Patent: Mar. 18, 2025

(54) ERYTHROPOIETIN-DERIVED PEPTIDES AND METHODS OF PROTECTING CELLS FROM OXIDATIVE DAMAGE INDUCED BY REACTIVE OXYGEN SPECIES

(71) Applicant: SYLUS CO., LTD., Jeonju-si (KR)

(72) Inventors: Che il Moon, Daegu (KR); Seung Jun Yoo, Gyeongsan-si (KR); Chang-Hun Lee, Daegu (KR); So Yeon Kim, Daegu (KR); Deok Ho Lee, Ansan-si (KR)

(73) Assignee: SYLUS CO., LTD., Jeonju-si (KR)

( * ) Notice: Subject to any disclaimer, the term of this patent is extended or adjusted under 35 U.S.C. 154(b) by 302 days.

(21) Appl. No.: 17/811,174

(22) Filed: Jul. 7, 2022

(65) Prior Publication Data
US 2022/0372094 A1 Nov. 24, 2022

Related U.S. Application Data

(60) Continuation of application No. 17/022,280, filed on Sep. 16, 2020, now abandoned, which is a division of
(Continued)

(30) Foreign Application Priority Data

Feb. 27, 2017 (KR) .................. 10-2017-0025370

(51) Int. Cl.
| | | |
|---|---|---|
| C07K 14/505 | (2006.01) | |
| A61K 38/00 | (2006.01) | |
| A61K 38/16 | (2006.01) | |
| A61K 38/17 | (2006.01) | |
| A61K 38/18 | (2006.01) | |
| C07K 7/00 | (2006.01) | |
| C07K 14/00 | (2006.01) | |
| C07K 14/435 | (2006.01) | |
| C07K 14/46 | (2006.01) | |
| C07K 14/47 | (2006.01) | |
| C07K 14/475 | (2006.01) | |
| C12N 15/86 | (2006.01) | |
| A61K 39/00 | (2006.01) | |
| A61K 47/64 | (2017.01) | |

(Continued)

(52) U.S. Cl.
CPC ........ *C07K 14/505* (2013.01); *A61K 38/1816* (2013.01); *C07K 14/4702* (2013.01); *C12N 15/86* (2013.01); *A61K 38/00* (2013.01); *A61K 38/1709* (2013.01); *A61K 38/179* (2013.01); *A61K 2039/55516* (2013.01); *A61K 2039/6031* (2013.01); *A61K 47/64* (2017.08); *A61K 2300/00* (2013.01); *A61P 9/00* (2018.01); *A61P 9/10* (2018.01); *A61P 21/00* (2018.01); *A61P 25/00* (2018.01); *A61P 25/02* (2018.01); *A61P 25/28* (2018.01); *C07K 7/08* (2013.01); *C07K 14/435* (2013.01); *C07K 14/47* (2013.01); *C07K 14/4705* (2013.01); *C07K 14/71* (2013.01); *C07K 2319/00* (2013.01); *C07K 2319/70* (2013.01); *C12N 15/85* (2013.01); *C12P 21/02* (2013.01); *G01N 33/5005* (2013.01); *G01N 33/5044* (2013.01); *G01N 33/5058* (2013.01); *G01N 33/68* (2013.01); *G01N 2800/52* (2013.01)

(58) Field of Classification Search
CPC ............. A61K 38/1816; A61K 38/00; A61K 2039/55516; A61K 38/1709; C07K 2319/00; C07K 14/505; C07K 14/435; C07K 14/47; C07K 14/00; C07K 14/475; A61P 25/00; A61P 25/28; A61P 25/02; A61P 9/00; A61P 9/10; A61P 29/00
See application file for complete search history.

(56) References Cited

U.S. PATENT DOCUMENTS

| | | | | |
|---|---|---|---|---|
| 8,329,652 B2 * | 12/2012 | Berezin | ................. | A61K 38/08 |
| | | | | 514/17.7 |
| 9,044,428 B2 * | 6/2015 | Berezin | ................. | A61K 38/07 |

(Continued)

FOREIGN PATENT DOCUMENTS

| | | | |
|---|---|---|---|
| EP | 3587443 A1 | 2/2018 | |
| KR | 20080094312 A | 10/2008 | |

(Continued)

OTHER PUBLICATIONS

Falkenburger et al., J. Neural. Transm, 2006; 70:261-268.*
Tayebati, Mech. Ageing Dev. 2006. 127: 100-8.*
Sarter, Neurosci. and Biobehav. Rev. 2004. 28: 645-650.*
Henstridge et al. Nat. Rev. Neurosci. 2019; 20: 94-107.*
Swerdlow, Clin. Interv. Ageing 2007; 2:347-359.*
Atwood et al., J. Alzheimer's Disease; 2015; 47:33-47.*
Anger. Neurotoxicology 1991. 12: 403-13.*
Blight Nat. Neurosci. 2002. 5: 1051-4.

(Continued)

*Primary Examiner* — Chang-Yu Wang
(74) *Attorney, Agent, or Firm* — CANTOR COLBURN LLP

(57) ABSTRACT

A peptide is described herein that has: (i) a simple structure compared to existing natural human erythropoietin, thus capable of easily passing through a tissue-blood barrier, (ii) excellent bioactivity with respect to cell-protecting activity, (iii) a low manufacturing cost, thus being economically advantageous, and (iv) no side effects on cell proliferation. Also, a pharmaceutical composition comprising the erythropoietin-derived peptide described herein as an active ingredient is described. The pharmaceutical composition may be used for preventing or treating cell damage-related illnesses, such as stroke, mechanical damage or ischemic damage to the nervous system, myocardial infarction, retinal damage, and diabetes. Also, the described pharmaceutical composition may be used for preventing cell damage.

7 Claims, 14 Drawing Sheets
Specification includes a Sequence Listing.

Related U.S. Application Data application No. 16/551,060, filed on Aug. 26, 2019, now Pat. No. 10,808,018, which is a continuation of application No. PCT/KR2018/002396, filed on Feb. 27, 2018.

(51) Int. Cl.

| | | |
|---|---|---|
| A61P 9/00 | (2006.01) | |
| A61P 9/10 | (2006.01) | |
| A61P 21/00 | (2006.01) | |
| A61P 25/00 | (2006.01) | |
| A61P 25/02 | (2006.01) | |
| A61P 25/28 | (2006.01) | |
| C07K 7/08 | (2006.01) | |
| C07K 14/71 | (2006.01) | |
| C12N 15/85 | (2006.01) | |
| C12P 21/02 | (2006.01) | |
| G01N 33/50 | (2006.01) | |
| G01N 33/68 | (2006.01) | |

(56) References Cited

U.S. PATENT DOCUMENTS

| | | | | |
|---|---|---|---|---|
| 10,808,018 | B2* | 10/2020 | Moon | C07K 7/06 |
| 11,566,056 | B2* | 1/2023 | Kim | A61P 25/28 |
| 11,987,608 | B2* | 5/2024 | Moon | C07K 14/505 |
| 2008/0260746 | A1* | 10/2008 | Abderrahim | A61P 25/28 424/139.1 |
| 2008/0260820 | A1 | 10/2008 | Borrelly et al. | |
| 2009/0197801 | A1* | 8/2009 | Berezin | A61K 38/07 435/375 |
| 2009/0221482 | A1 | 9/2009 | Cerami et al. | |
| 2013/0123174 | A1* | 5/2013 | Berezin | A61K 38/10 514/8.3 |
| 2014/0378378 | A1* | 12/2014 | Kim | A61P 25/28 530/326 |
| 2015/0238556 | A1* | 8/2015 | Berezin | A61P 25/16 514/17.7 |
| 2019/0135913 | A1 | 5/2019 | Ghosh et al. | |
| 2019/0375810 | A1* | 12/2019 | Moon | C07K 14/4702 |
| 2021/0371484 | A1* | 12/2021 | Kim | C07K 14/505 |

FOREIGN PATENT DOCUMENTS

| | | |
|---|---|---|
| KR | 101148191 B1 | 5/2012 |
| KR | 1020150090101 A | 8/2015 |
| WO | 200219963 A2 | 3/2002 |
| WO | 200220034 A1 | 3/2002 |
| WO | 2006119767 A | 11/2006 |
| WO | 2006120030 A | 11/2006 |
| WO | 2007120614 A2 | 10/2007 |
| WO | 2018155997 A1 | 8/2018 |
| WO | WO-2020045886 A1 * | 3/2020 ............. A23L 33/18 |

OTHER PUBLICATIONS

Dmytriyeva, O., et al., "Epobis is a Nonerythropoietic and Neuroprotective Agonist of the Erythropoietin Receptor with Anti-Inflammatory and Memory Enhancing Effects," Mediators of Inflammation, Article ID 1346390, 11 pages (2016).
English Translation of Office Action dated Dec. 1, 2020 of Japanese Patent application No. 2019-546386.
Extended European search report dated Jan. 18, 2021 of European Patent Application No. 18756838.1.
GenBank: ANC33499.2, "1 OF7-linker-EPO(K45D), partial [synthetic construct], "XP055537041, retrieved from NCBI Database accession No. ANC33499.2 (Jun. 24, 2016).
Hoke et al. Nat. Clin. Pract. Neural. 2006: 448-454.
International Search Report (and English translation) received in PCT Application No. PCT/KR2018/002396 dated Jun. 4, 2018.
Office Action dated Dec. 1, 2020 of Japanese Patent application No. 2019-546386.
Pankratova, S. et al., A new agonist of the erythropoietin receptor, Epobis, induces neurite outgrowth and promotes neuronal survival, J. Neurochem., (2012), vol. 121, No. 6, pp. 915-923.
Pankratova, S., et al., "Neuroprotective properties of a novel, non-haematopoietic agonist of the erythropoietin receptor," Brain, 133:2281-2294 (2010).
Partial supplementary European search report dated Oct. 12, 2020 of European Patent Application No. 18756838.1.
Schmidt et al. Annu. Rev. Biomed. Eng. 2003. 5: 293-347.
Syed etal., Nature, 1998; 395:511-516.
Sytkowski, A.J., et al., "Immunochemical Studies of Human Erythropoietin UsingSite-specific Anti-peptide Antibodies," The Journal of Biological Chemistry,262(3) : 1161-1165 (1987).
Written Opinion received in PCT Application No. PCT/KR2018/002396 dated Jun. 4, 2018 in Korean language.
Yoo, S-J, et al., "Neuroprotective Effects of an Erythropoietin-Derived Peptide in PC12 Cells under Oxidative Stress," CNS & Neurological Disorders, Drug Targets, 15:927-934 (2016).
Yu, H.M. et al., Role of the JAK-STAT pathway in protection of hydrogen peroxide preconditioning against apoptosis induced by oxidative stress in PC12 cells, Apoptosis, (2006), vol. 11, pp. 931-941.

* cited by examiner

FIG. 1C
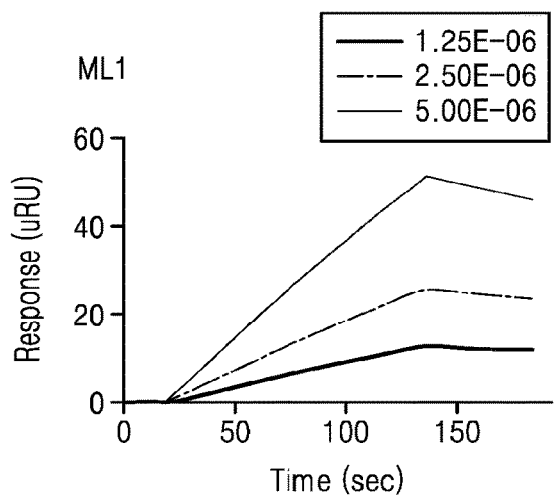
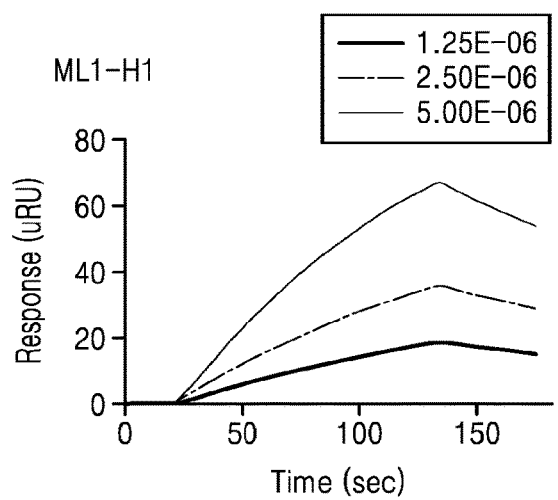
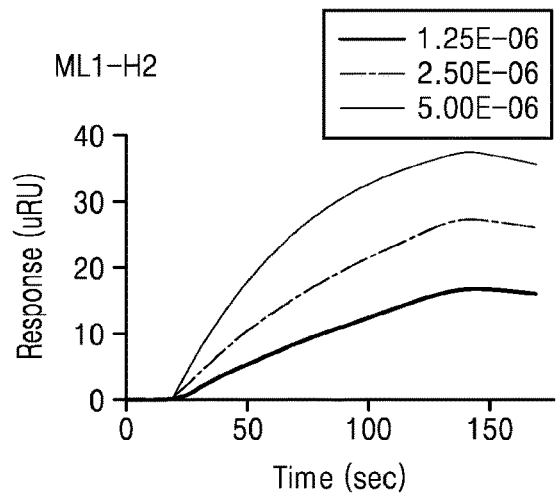
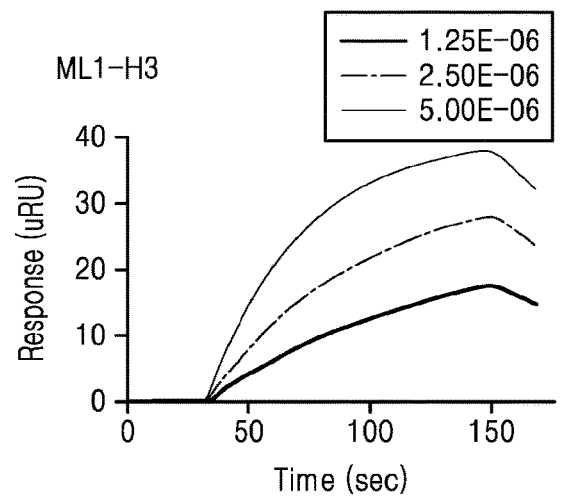

FIG. 2D
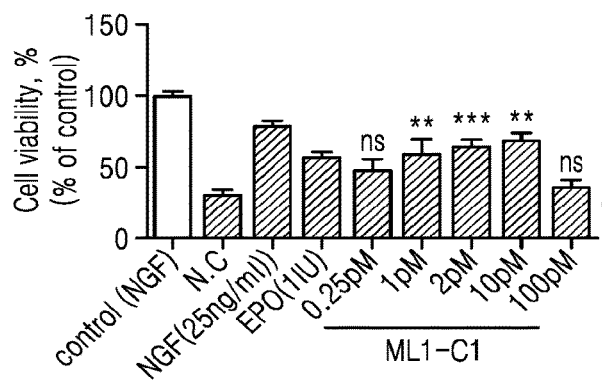
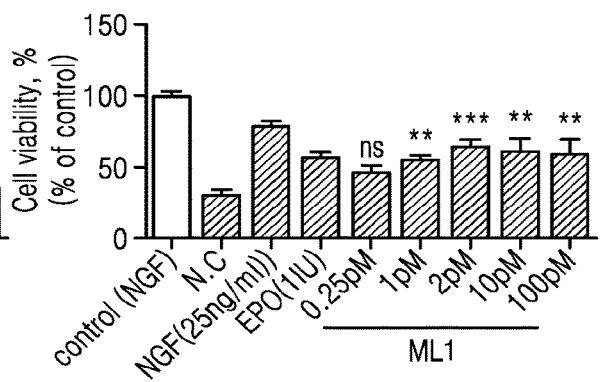
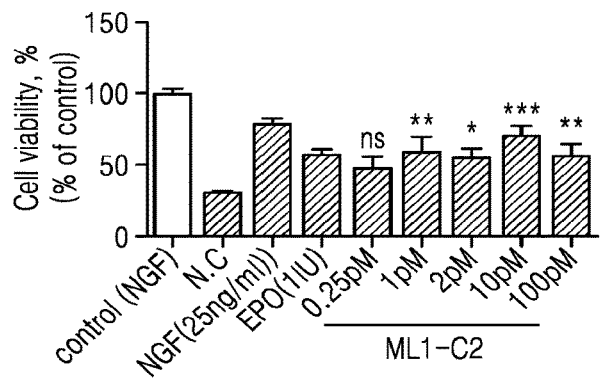
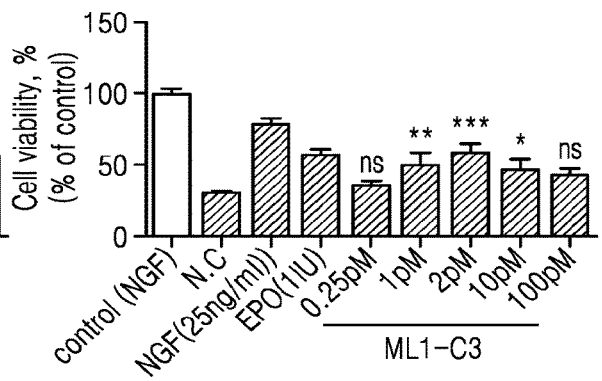

FIG. 5
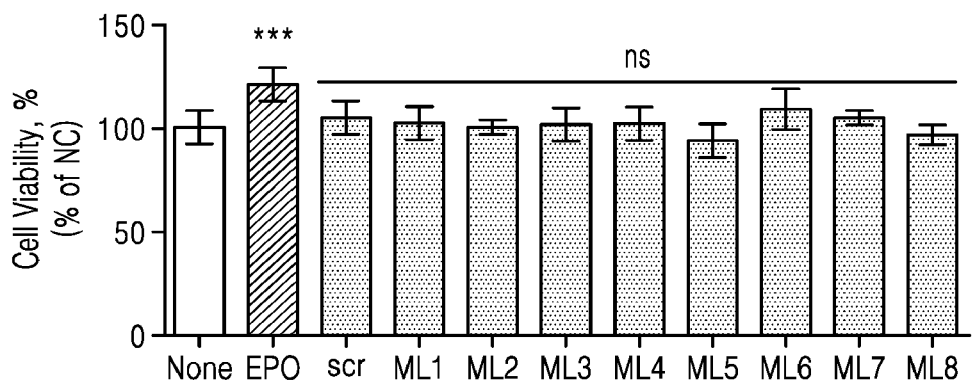
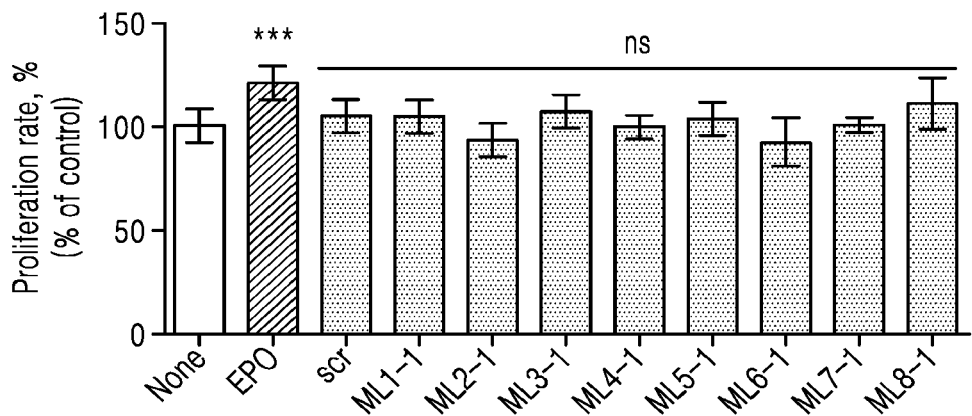
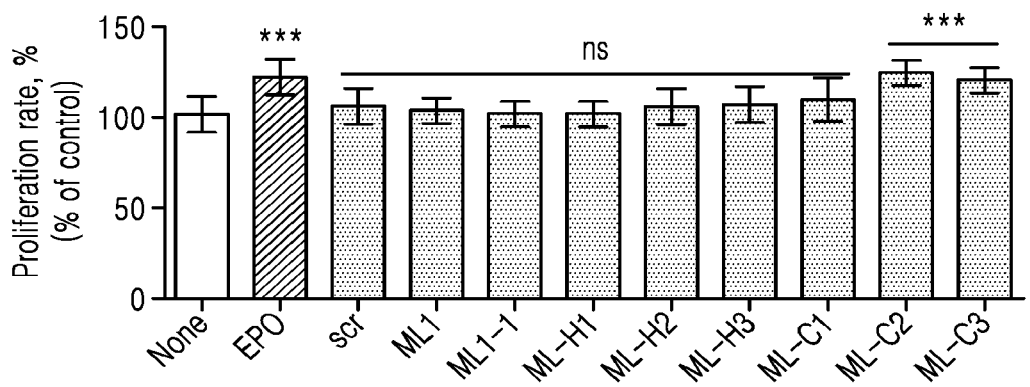

FIG. 6

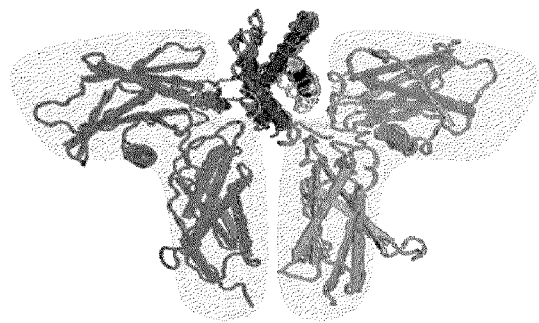

Structral studies of EPOR & EPO (crystal structure of the EPO:EPOR2 complex)

Site 1
High-affinity binding site
(helix D-AB loop interface)
Key amino acid
- helix D : Asn 147, Arg 150, Gly 151
- AB loop : Thr 41-Lys 52
(Syed et al., Nature 1998)

Site 1
low-affinity binding site
(helix C)
Key amino acid
Arg103, Ser104, Leu105, Leu108 and Arg110
(Syed et al., Nature 1998)

target site according to the present invention erythropoietin-derived peptide

ERYTHROPOIETIN-DERIVED PEPTIDES AND METHODS OF PROTECTING CELLS FROM OXIDATIVE DAMAGE INDUCED BY REACTIVE OXYGEN SPECIES

RELATED APPLICATIONS

This application is a continuation application of U.S. patent application Ser. No. 17/022,280, filed Sep. 16, 2020, which is a divisional application of U.S. patent application Ser. No. 16/551,060, filed Aug. 26, 2019, now U.S. Pat. No. 10,808,018, which is a continuation application of International Application No. PCT/KR2018/002396, filed Feb. 27, 2018, which claims priority from Korean Patent Application No. 10-2017-0025370, filed on Feb. 27, 2017, the disclosure of each of which is hereby incorporated by reference herein in its entirety.

SEQUENCE LISTING

This application is being filed electronically via EFS-Web and includes an electronically submitted Sequence Listing in .txt format. The .txt file contains a sequence listing entitled "16458_7_Seq_Listing_ST25" created on Aug. 23, 2019 and is 8000 bytes in size. The sequence listing contained in this .txt file is part of the specification and hereby incorporated by reference in its entirety.

BACKGROUND

The present disclosure relates to an erythropoietin (EPO)-derived peptide of which a side effect of cell proliferation is eliminated, and a pharmaceutical composition for preventing or treating a neurodegenerative disease, the pharmaceutical composition including the EPO-derived peptide.

During lifetime, the human body is consistently exposed to stimuli which are harmful to the human body. In response to such exposure, the individual protects their body. Harmful stimuli include various stimuli such as hypoxia, infection, mechanical stimulations, etc. Defense mechanisms against such stimuli exist at a cellular level. Various cytokines that are secreted as a defense mechanism against stimuli play a role in protecting an individual by killing abnormal cells produced due to exposure to stimuli or by preventing death of normal cells.

Erythropoietin (EPO) is a glycoprotein having a molecular weight of about 30,000, and is a hematopoietic cytokine which promotes differentiation of red blood cell precursors and increases the number of red blood cells to exhibit an effect of preventing or improving anemia. This protein initiates its function by binding to a receptor of red blood cell precursors and induces an increase in intracellular calcium ions, an increase in DNA biosynthesis, stimulation of hemoglobin production, etc. Therefore, EPO may be used as a therapeutic agent for anemia such as anemia in patients with a renal disease, anemia in premature babies, anemia associated with hypothyroidism, anemia associated with malnutrition, anemia associated with chronic renal failure, postoperative anemia, etc.

Beyond anemia management, EPO has been recently considered as a therapeutic agent for neurological damage. EPO has exhibited tissue protective ability with respect to nervous system damage, and has also exhibited an effect of reducing tissue damage in an animal model of acute myocardial infarction.

However, in addition to the therapeutic effect on anemia and the ability to protect nerve cells and nervous tissue, it has been found that an increase in red blood cells and an increase in platelet activity may occur when EPO is injected into the human body. These adverse effects may lead to a decrease in the tissue protective ability of EPO. Accordingly, research is being conducted into the development of modified EPO or peptides including a partial structure of EPO such as asialo-EPO, carbamylated EPO, EPOtris, EPObis, etc., which are capable of maintaining the tissue protective ability without increasing red blood cells or stimulating platelet activity.

As described above, EPO is known to have a therapeutic effect on anemia, an ability to protect nerve cells or nervous tissue, and an ability to protect myocardial tissue. EPO is a very active protein, but has a very high production cost. When EPO is injected into peripheral blood vessels, EPO may not be transported to a target organ due to a tissue-blood barrier present in certain target organs, which causes difficulties in drug delivery. Accordingly, there is a need for an effective human EPO substitute having low production costs and capable of being easily transported to biological tissues.

Accordingly, the present inventors have prepared a human erythropoietin-derived peptide having lower production costs than natural erythropoietin and the ability to easily pass through the tissue-blood barrier in the body while maintaining the cell or tissue protective abilities of natural human erythropoietin without inducing the side effect of cell proliferation, thereby completing the present disclosure.

SUMMARY

An aspect provides a peptide which is described by any one amino acid sequence selected from the group consisting of SEQ ID NOS: 1 to 25.

Another aspect provides a pharmaceutical composition for preventing or treating a neurodegenerative disease, the pharmaceutical composition including, as an active ingredient, the peptide, one or more polynucleotides encoding the peptide, a vector including the polynucleotide, or a host cell including the vector.

Still another aspect provides a method of preventing or treating a neurodegenerative disease, the method including administering the composition including, as an active ingredient, the peptide, one or more polynucleotides encoding the peptide, the vector including the polynucleotide, or the host cell including the vector.

Still another aspect provides use of the composition including, as an active ingredient, the peptide, one or more polynucleotides encoding the peptide, the vector including the polynucleotide, or the host cell including the vector in the preparation of a prophylactic or therapeutic agent for a neurodegenerative disease.

BRIEF DESCRIPTION OF DRAWINGS

FIG. 1 shows graphs showing binding affinities measured by a surface plasmon resonance (SPR) technique to determine whether erythropoietin-derived peptides act on the erythropoietin receptor:

FIG. 1C: determination of binding affinities of ML1, ML1-H1, ML1-H2, and ML1-H3.

Figure 2A:
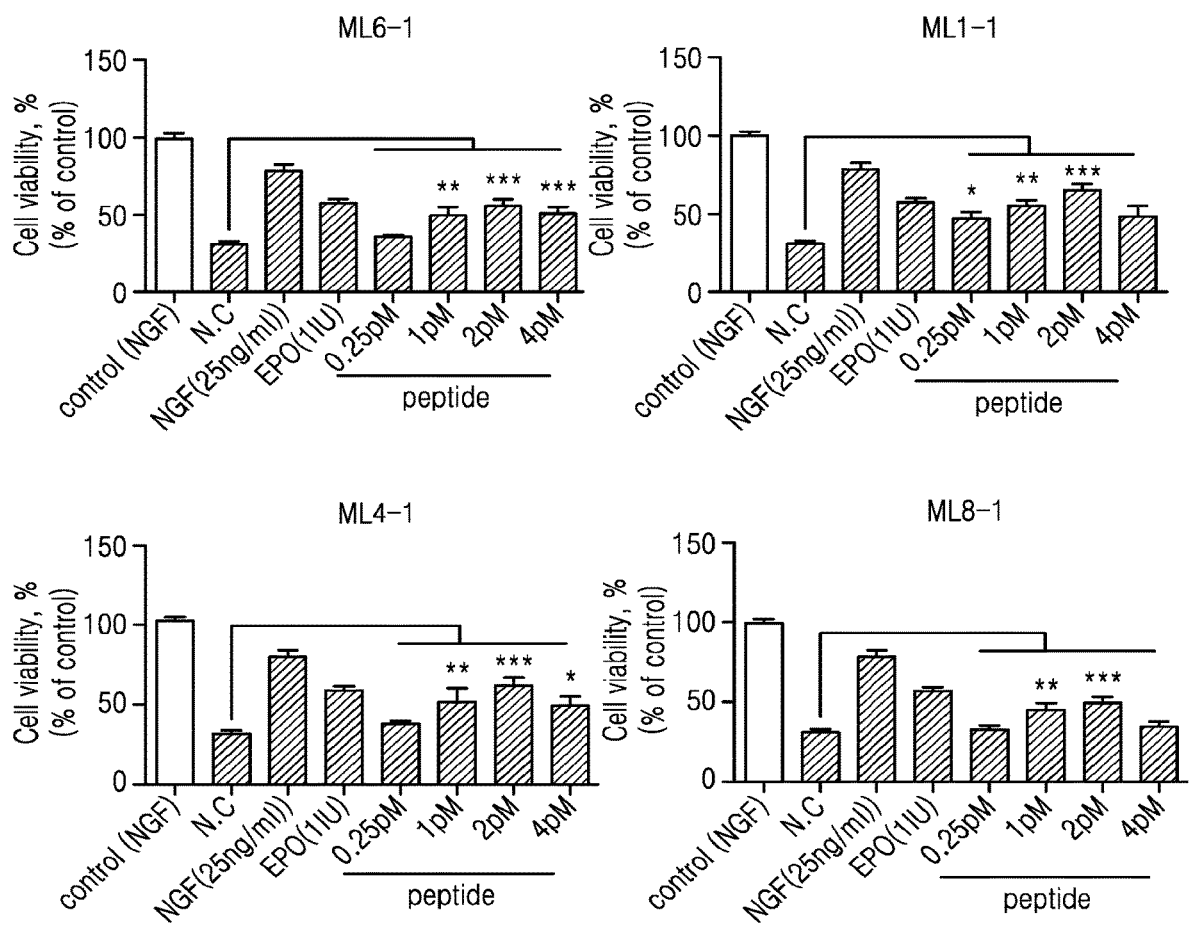
FIG. 2A: effects of treatment with ML1-1, ML4-1, ML6-1, and ML8-1.
Figure 2B:
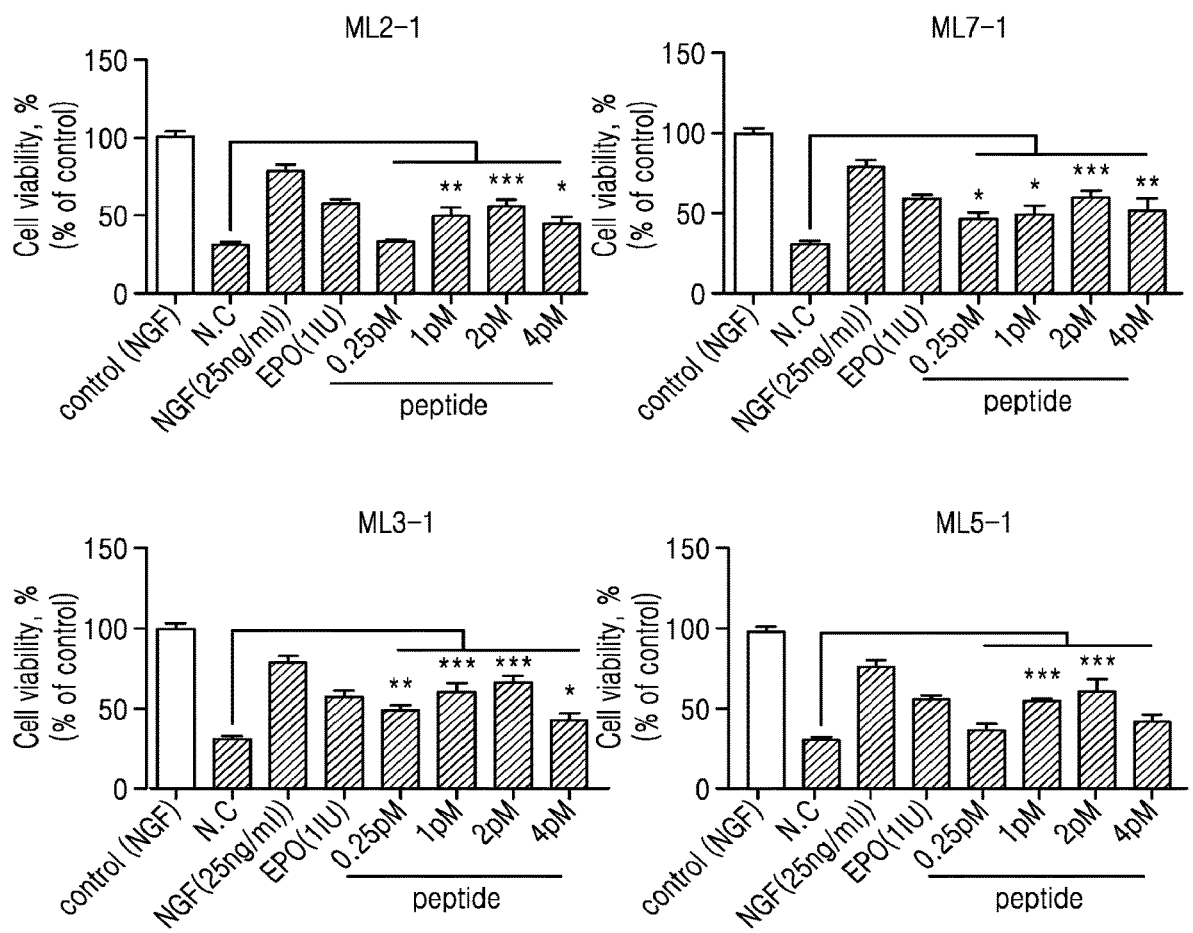
FIG. 2B: effects of treatment with ML2-1, ML3-1, ML5-1, and ML7-1.
Figure 2C:
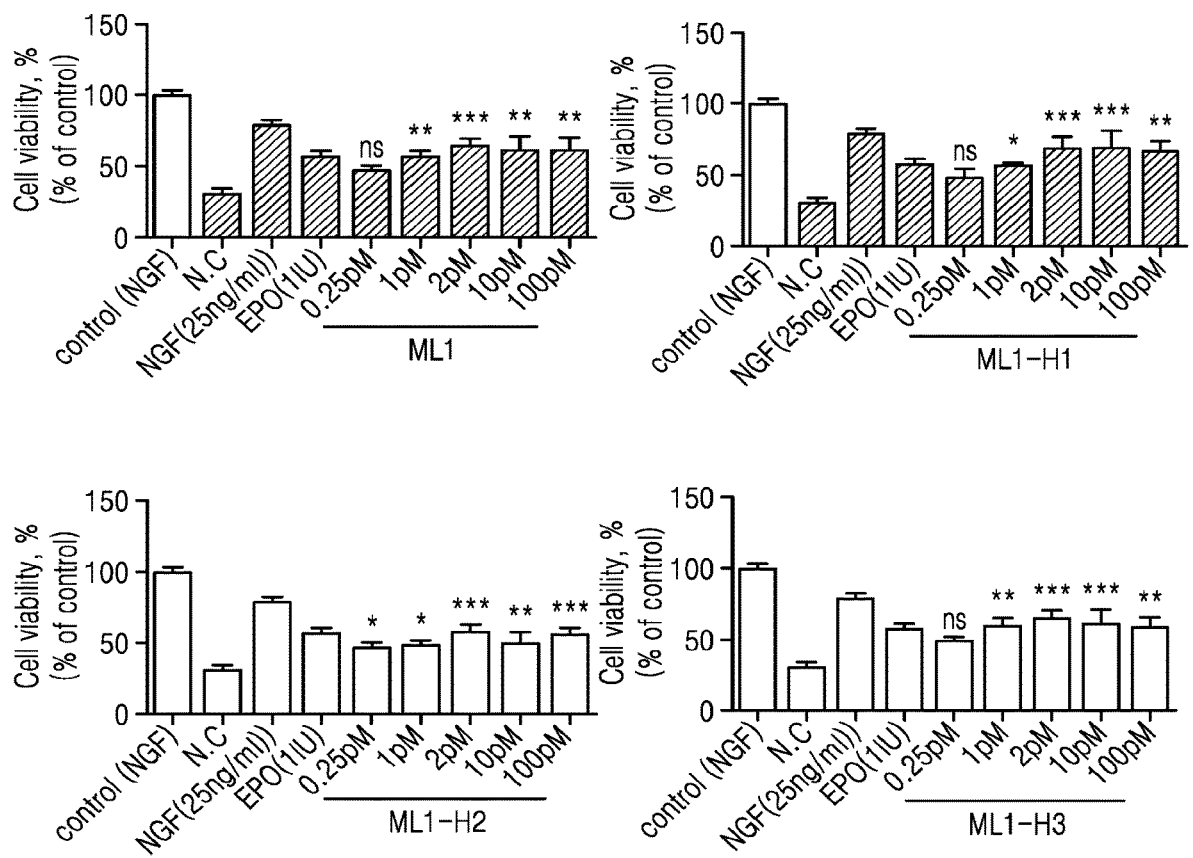
FIG. 2 shows graphs showing cell protective effects of erythropoietin-derived peptide treatment of cells in which reactive oxygen species were increased by hydrogen peroxide.
Figure 3A:
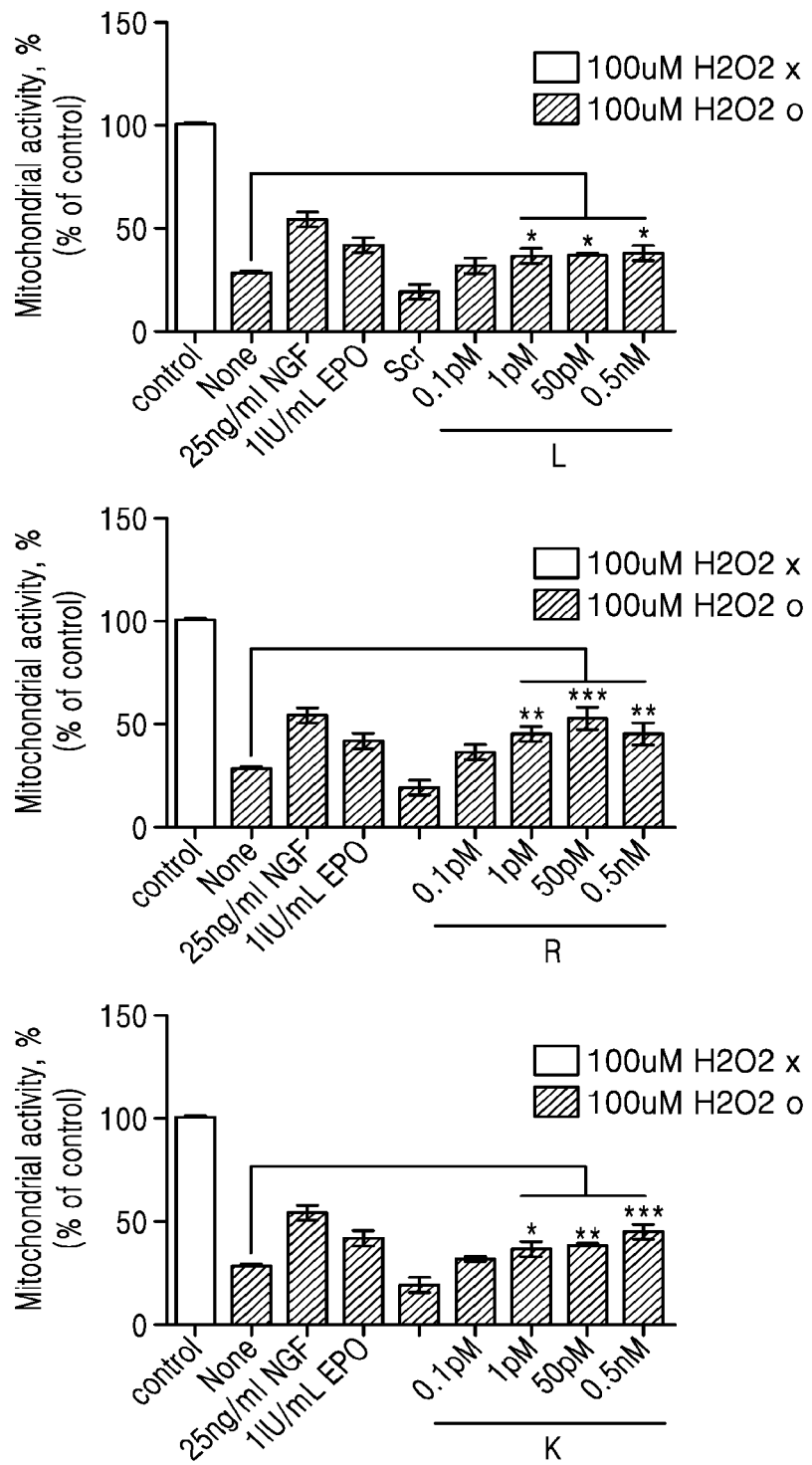
Figure 3B:
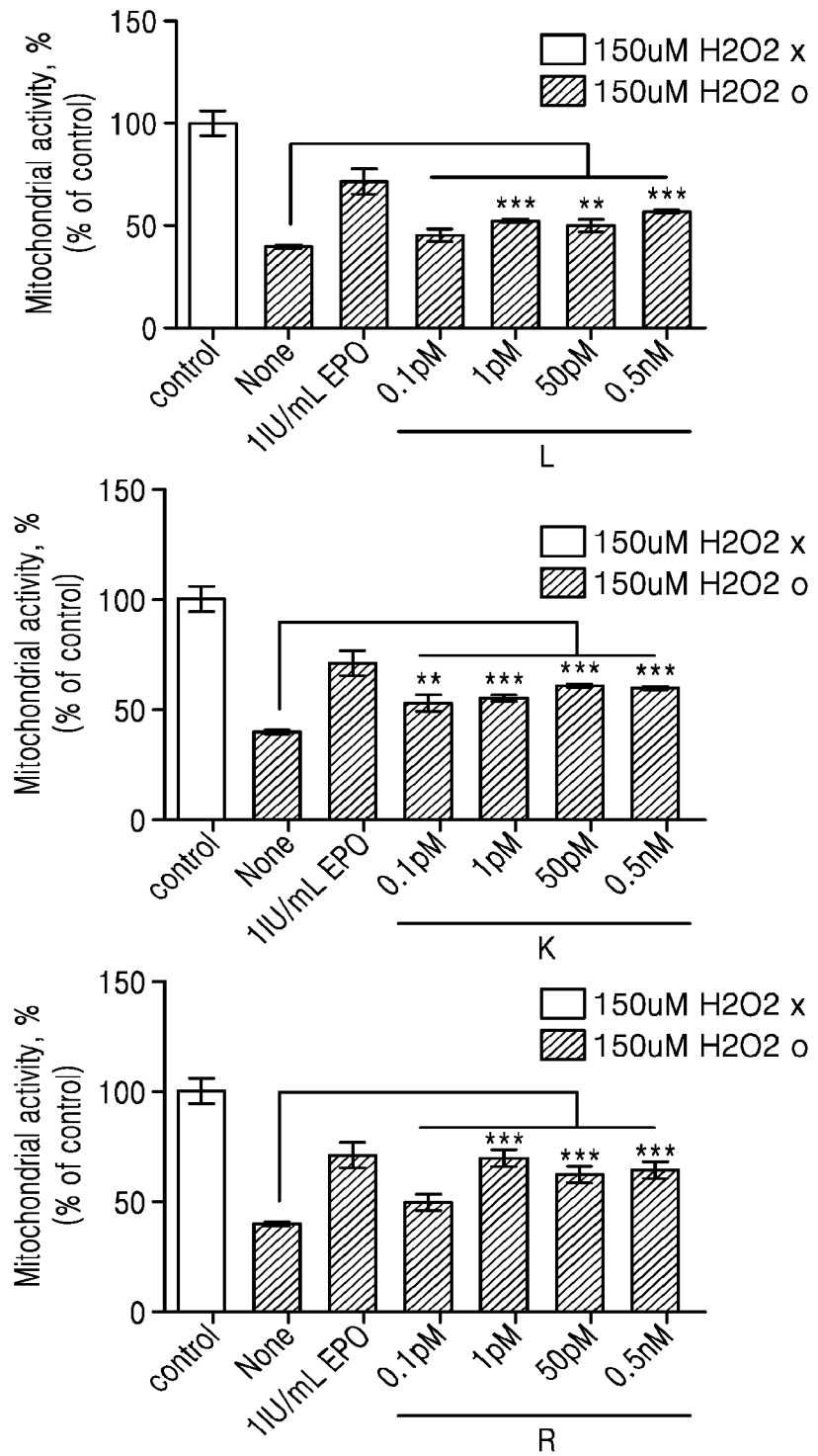
Figure 4:
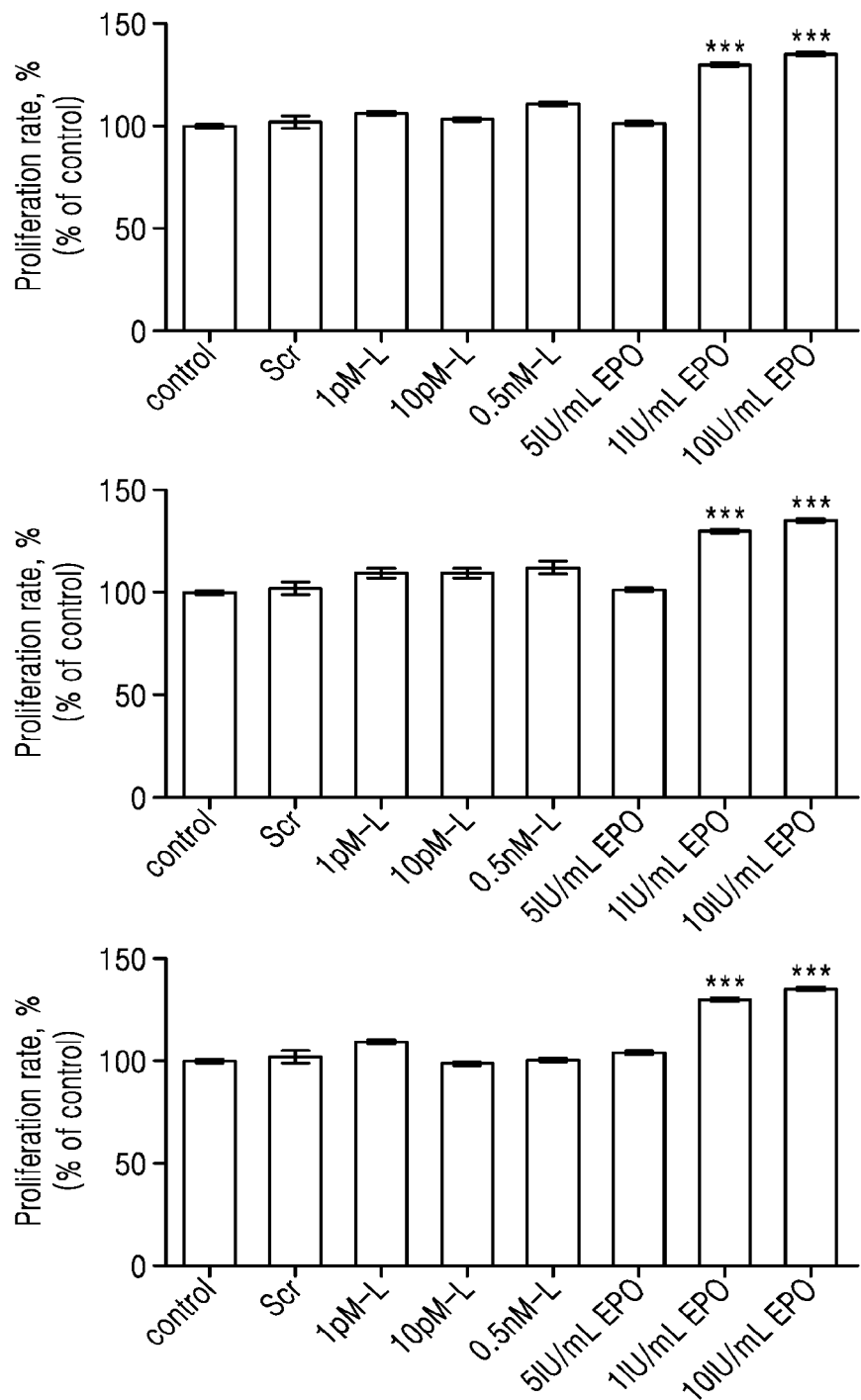
Figure 7:
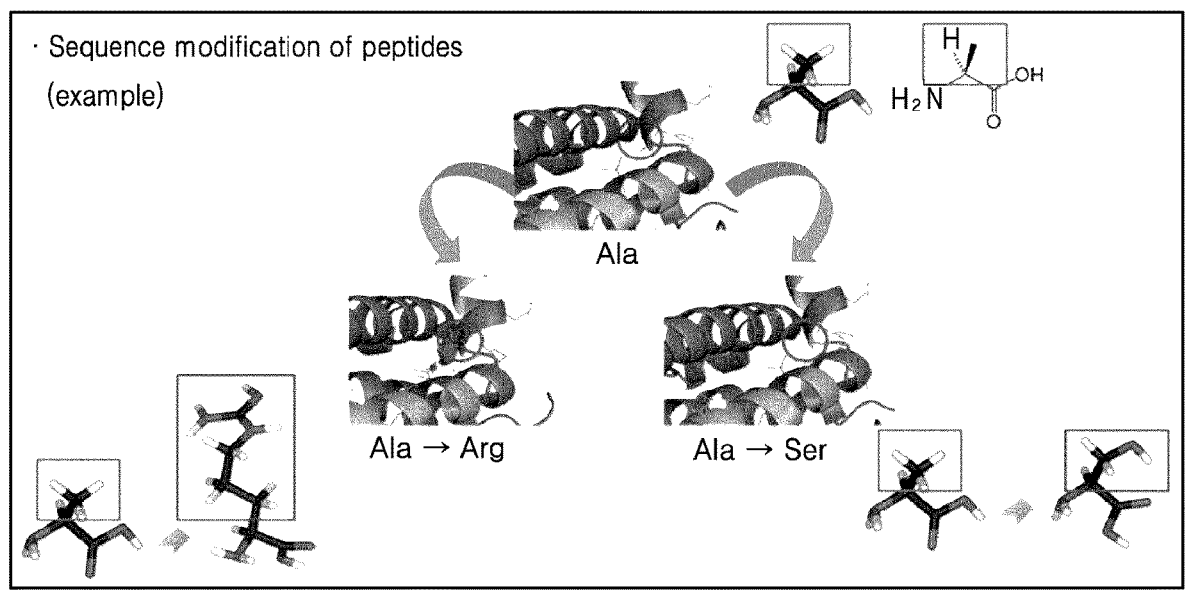

Control (NGF): cells treated with nerve growth factor (NGF) as a control group,

N.C: cells treated with hydrogen peroxide,

NGF (25 ng/ml): cells treated with NGF after treatment with hydrogen peroxide,

EPO (1 IU): an experimental group treated with 1 IU/ml of natural erythropoietin after treatment with hydrogen peroxide, 0.25 pM: an experimental group treated with 0.25 pM of the peptide of the present disclosure after treatment with hydrogen peroxide, 1 pM: an experimental group treated with 1 pM of the peptide of the present disclosure after treatment with hydrogen peroxide, 2 pM: an experimental group treated with 2 pM of the peptide of the present disclosure after treatment with hydrogen peroxide, 4 pM: an experimental group treated with 4 pM of the peptide of the present disclosure after treatment with hydrogen peroxide, FIG. 2C: effects of treatment with ML1, ML1-H1, ML1-H2, and ML1-H3, FIG. 2D: effects of treatment with ML1, ML1-C1, ML1-C2, and ML1-C3, Control (NGF): cells treated with NGF as a control group, N.C: cells treated with hydrogen peroxide, NGF (25 ng/ml): cells treated with NGF after treatment with hydrogen peroxide, EPO (1 IU): an experimental group treated with 1 IU/ml of natural erythropoietin after treatment with hydrogen peroxide, 0.25 pM: an experimental group treated with 0.25 pM of the peptide of the present disclosure after treatment with hydrogen peroxide, 1 pM: an experimental group treated with 1 pM of the peptide of the present disclosure after treatment with hydrogen peroxide, 2 pM: an experimental group treated with 2 pM of the peptide of the present disclosure after treatment with hydrogen peroxide, 10 pM: an experimental group treated with 10 pM of the peptide of the present disclosure after treatment with hydrogen peroxide, and 100 pM: an experimental group treated with 100 pM of the peptide of the present disclosure after treatment with hydrogen peroxide;

FIG. 3 shows graphs showing cell protective effects of peptides (ML1-L2, ML1-K2, and ML1-R2) prepared by partially modifying sequences of an erythropoietin-derived ML1 peptide:

FIG. 3A: cell protective effects in differentiated PC12 cells,

FIG. 3B: cell protective effects in human SH-SY5Y cells,

Control: non-treated cells as a control group,

None: cells treated with hydrogen peroxide,

NGF (25 ng/ml): cells treated with NGF after treatment with hydrogen peroxide, as a positive control group, EPO (1 IU/mL): an experimental group treated with 1 IU/ml of natural erythropoietin after treatment with hydrogen peroxide, Scr: cells treated with 1 pM of scrambled (Scr) peptide after treatment with hydrogen peroxide, as a negative control group, 0.1 pM: an experimental group treated with 0.1 pM of the peptide of the present disclosure after treatment with hydrogen peroxide, 1 pM: an experimental group treated with 1 pM of the peptide of the present disclosure after treatment with hydrogen peroxide, 50 pM: an experimental group treated with 50 PM of the peptide of the present disclosure after treatment with hydrogen peroxide, and 0.5 nM: an experimental group treated with 0.5 nM of the peptide of the present disclosure after treatment with hydrogen peroxide;

FIG. 4 shows graphs showing cell proliferation rates of peptides (ML1-L2, ML1-K2, and ML1-R2) prepared by partially modifying sequences of the erythropoietin-derived ML1 peptide:

Control: non-treated cells as a control group,

Scr: cells treated with 1 pM of Scr peptide after treatment with hydrogen peroxide, as a negative control group, 1 pM: an experimental group treated with 1 pM of the peptide of the present disclosure, 50 pM: an experimental group treated with 50 pM of the peptide of the present disclosure, 0.5 nM: an experimental group treated with 0.5 nM of the peptide of the present disclosure, 0.5 IU/mL EPO: an experimental group treated with 0.5 IU/ml of natural erythropoietin, 1 IU/mL EPO: an experimental group treated with 1 IU/ml of natural erythropoietin, and 10 IU/mL EPO: an experimental group treated with 10 IU/ml of natural erythropoietin;

FIG. 5 shows graphs showing cell proliferative effects of the erythropoietin-derived peptides and peptides prepared by partially modifying sequences thereof;

FIG. 6 shows an illustration of a structure of a complex of erythropoietin receptor (EPOR) and erythropoietin (EPO) of one embodiment and binding target sites; and FIG. 7 shows an illustration of a substitution process of amino acid sequences of one embodiment.

DESCRIPTION

An aspect provides a peptide which is described by any one amino acid sequence selected from the group consisting of SEQ ID NOS: 1 to 25.

The peptide may be derived from an erythropoietin protein sequence. The peptide may bind to an erythropoietin receptor and may form an alpha-helical structure.

The peptide may exhibit cell protective activity and may have no side effect of cell proliferation.

The peptide of one embodiment may bind to a target site 1 or a target site 2 of an erythropoietin receptor.

The erythropoietin receptor (EPOR) has two target sites, through which EPOR forms a complex with erythropoietin (EPO). According to previous studies, of the two binding target sites, the target site 1 forms a strong bond (KD=~1 nM) and the target site 2 forms a weak bond (KD=~1 μM) (see FIG. 6).

The target site targeted in the present disclosure is a weak binding site, and the weak binding of EPOR and the peptide of the present disclosure may prevent the side effect (proliferative effect) which is induced by binding of natural EPO to EPOR thereof. Arg103, Ser104, Leu105, Leu108, and Arg110 are known as crucial amino acid sequences in EOPR, and based on EPO sequences directly binding to these sequences, the target site was determined.

In one embodiment, the present inventors synthesized peptides from a partial target site of natural EPO according to a known solid phase peptide synthesis technology, and specific characteristics of the respective peptides were identified (see Tables 1 and 2). Further, "LHVDKAVSGLRSLTTL" which is part of a basic sequence of ML1 was used to prepare peptides having modified amino acids at both ends thereof (see Table 7).

Figure 1A:
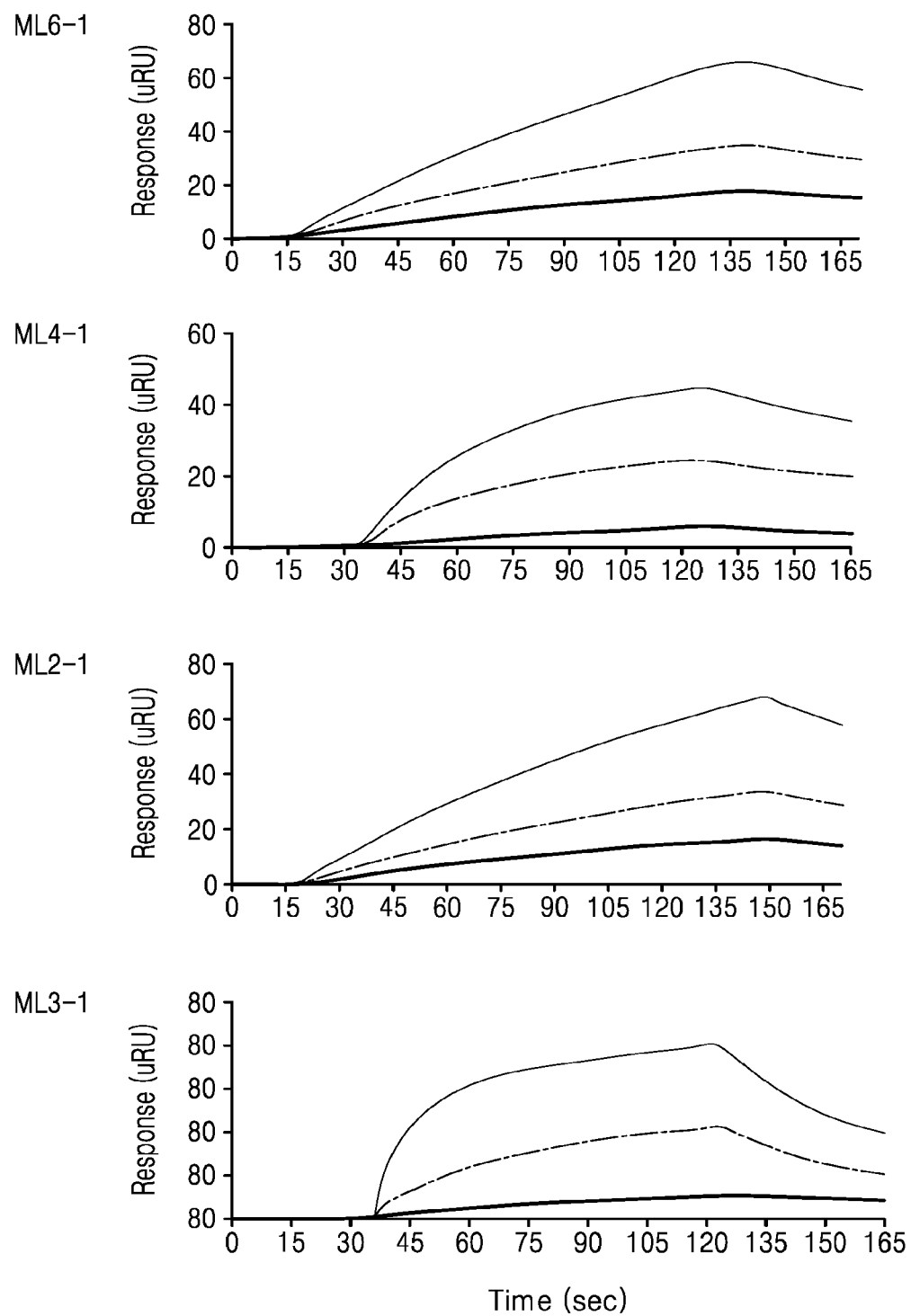
FIG. 1A: determination of binding affinities of ML6-1, ML4-1, ML2-1, and ML3-1.
Figure 1B:
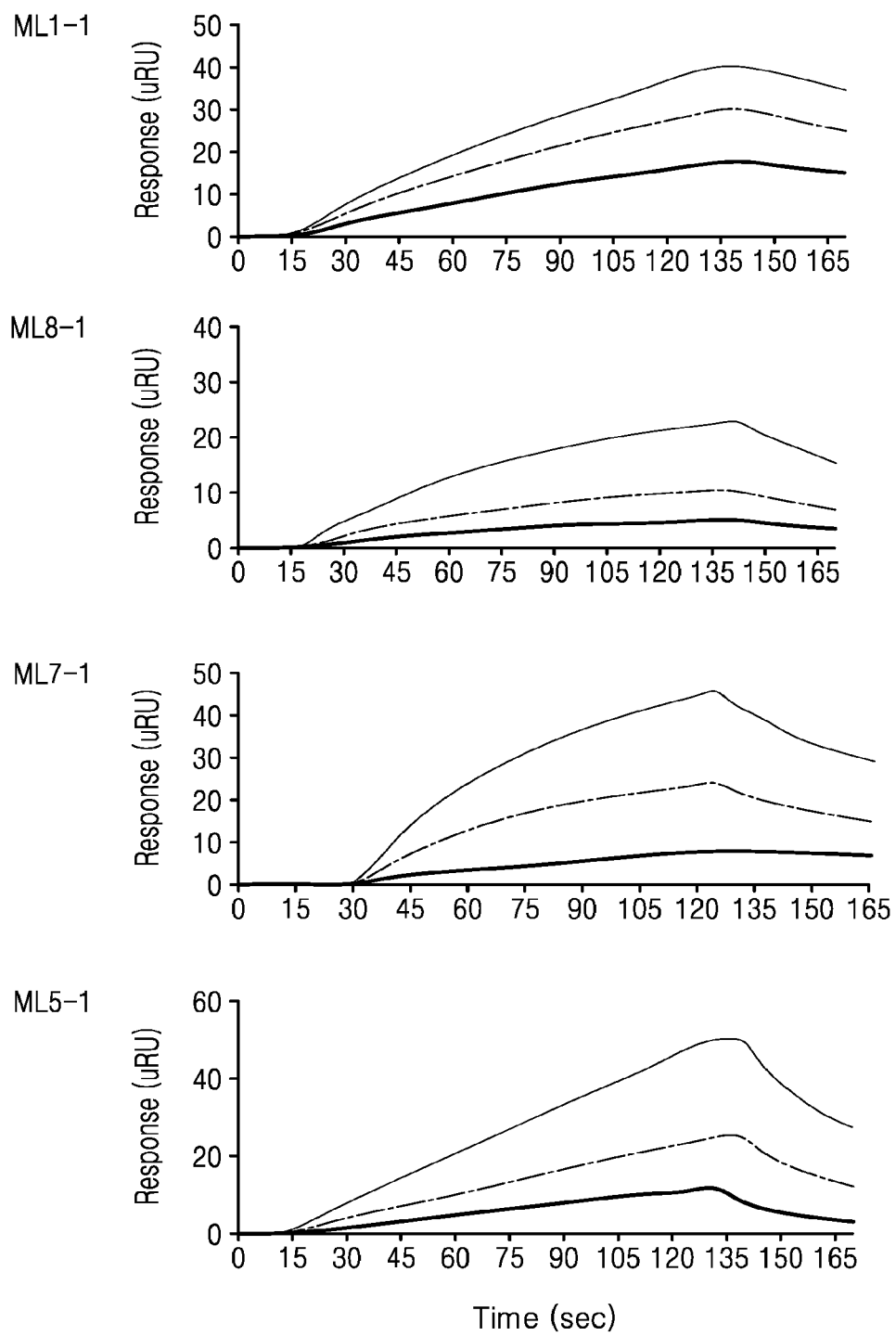
FIG. 1B: determination of binding affinities of ML1-1, ML8-1, ML7-1, and ML5-1.
Figure 1D:
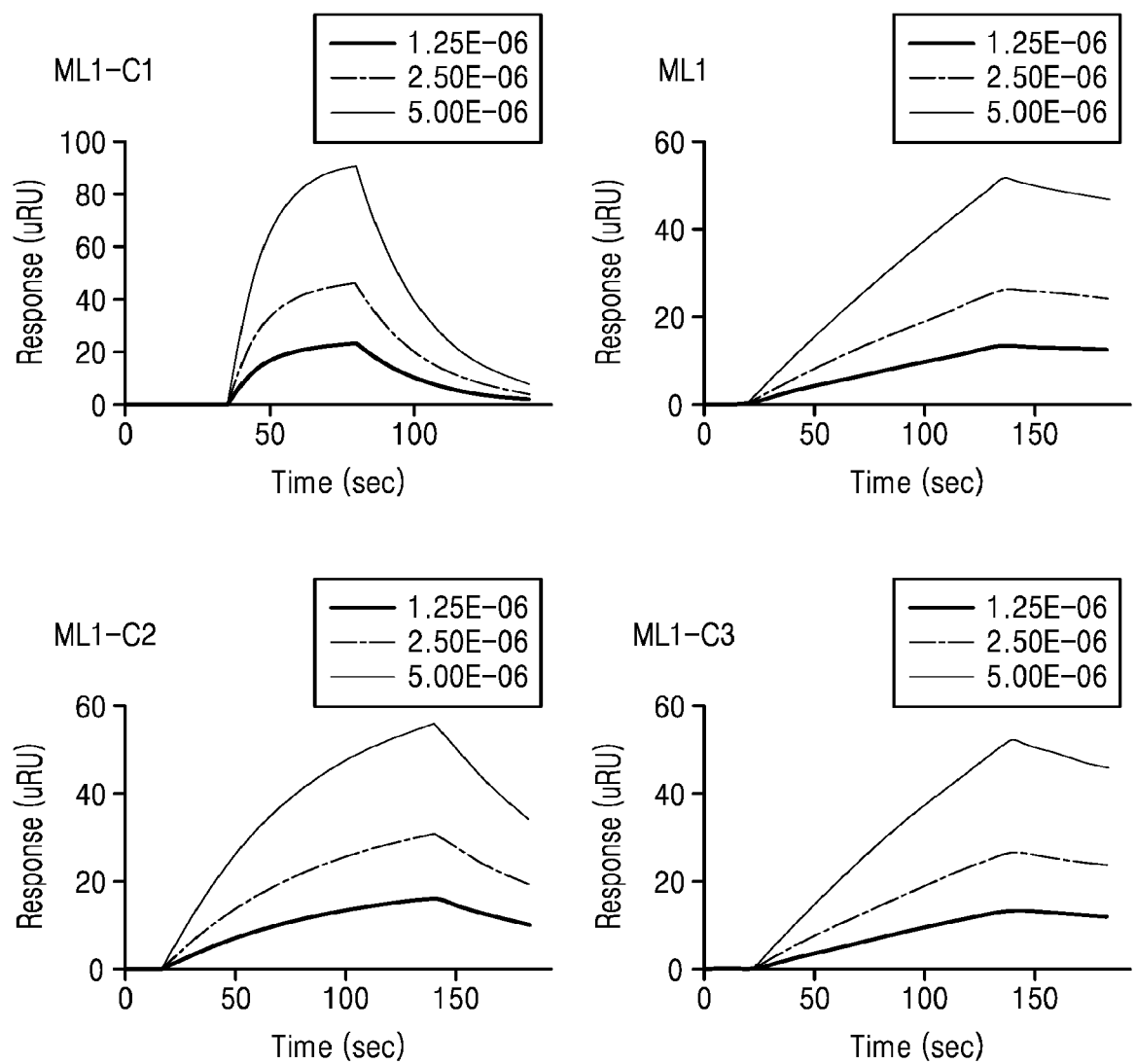
FIG. 1D: determination of binding affinities of ML1, ML1-C1, ML1-C2, and ML1-C3.

The present inventors confirmed that the peptides of the present disclosure may bind to EPOR to exert their actions (see FIG. 1, and Tables 8 and 9). The present inventors also confirmed that the erythropoietin-derived peptides prepared in the present disclosure may form a stable alpha-helix like natural EPO.

The present inventors confirmed that cells under stress environments induced by increased reactive oxygen species due to hydrogen peroxide may be protected by treatment with the erythropoietin-derived peptide prepared in the present disclosure (see FIGS. 2 and 3). The present inventors confirmed that inhibition of mitochondrial activity under stress environments induced by increased reactive oxygen species due to hydrogen peroxide may be suppressed by treatment with the erythropoietin-derived peptide prepared in the present disclosure (see FIG. 3). The present inventors confirmed that the peptides (ML1-L2, ML1-K2, and ML1-R2) prepared in the present disclosure have no side effect of cell proliferation (see FIG. 4).

Accordingly, the peptides of the present disclosure may bind to EPOR and may inhibit cell death without the side effect of cell proliferation, thereby being usefully applied as an EPO substitute to the prevention or treatment with neurodegenerative diseases.

Another aspect provides a pharmaceutical composition for preventing or treating a neurodegenerative disease, the pharmaceutical composition including, as an active ingredient, the peptide described by any one amino acid sequence selected from the group consisting of SEQ ID NOS: 1 to 25, one or more polynucleotides encoding the peptide, a vector including the polynucleotide, or a host cell including the vector.

The composition may exhibit cell protective activity and may have no side effect of cell proliferation.

The neurodegenerative disease may be selected from the group consisting of stroke, paralysis, myocardial infarction, dementia, Alzheimer's disease, Parkinson's disease, multiple sclerosis, Huntington's disease, Pick's disease, and Creutzfeldt-Jakob disease.

The host cell may be an HEK-293E cell, a Chinese hamster ovary (CHO) cell, a baby hamster kidney (BHK) cell, an NIH-3T3 cell, an HEK-293T cell, or a COS-7 cell.

The vector may be selected from the group consisting of a linear DNA vector, a plasmid DNA vector, or a recombinant viral vector. The recombinant virus may be selected from the group consisting of retroviruses, adenoviruses, adeno-associated viruses, herpes simplex viruses, and lentiviruses.

A therapeutically effective dose of the composition may vary depending on various factors, for example, an administration method, a target area, a patient's conditions, etc. Thus, when the composition is used in the human body, the administration dose is required to be suitably determined by taking into consideration both safety and efficiency. It is also possible to estimate the dose for human administration from the effective dose determined through an animal test. Such considerations to be taken into the determination of the effective dose are described, for example, in Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The composition may also include a carrier, a diluent, an excipient, or a combination of two or more thereof, which are commonly used in biological formulations. The pharmaceutically acceptable carrier is not particularly limited, as long as it is suitable for in vivo delivery of the composition. For example, the compounds described in Merck Index, 13th ed., Merck & Co. Inc., physiological saline, sterile water, Ringer's solution, buffered saline, a dextrose solution, a maltodextrin solution, glycerol, ethanol, and a mixture of one or more of these components may be used. If necessary, the composition may include other common additives such as antioxidants, buffers, bacteriostatic agents, etc.

In addition, the composition may be prepared into injectable formulations, such as aqueous solutions, suspensions, and emulsions, pills, capsules, granules, or tablets, by adding diluents, dispersing agents, surfactants, binders, and lubricants thereto. Furthermore, the composition may be appropriately formulated according to each disease or component by a suitable method known in the art or by using a method disclosed in Remington's Pharmaceutical Science (Mack Publishing Company, Easton PA, 18th, 1990).

The composition may further include one or more active ingredients having identical or similar functions. The composition may include the protein in an amount of 0.0001% by weight to 10% by weight, or 0.001% by weight to 1% by weight, based on the total weight of the composition.

The composition may be administered parenterally (e.g., intravenous, subcutaneous, intraperitoneal, or topical application) or orally according to the intended method. The administration dose may vary depending on a patient's weight, age, sex, health conditions, diet, administration time, administration method, excretion rate, and severity of the disease. A daily dose of the composition may 0.0001 mg/ml to 10 mg/ml or 0.0001 mg/ml to 5 mg/ml, and the composition may be administered once or several times a day.

The vector including the polynucleotide encoding the peptide may be included in an amount of 0.05 mg to 500 mg or 0.1 mg to 300 mg, and the recombinant virus including the polynucleotide encoding the peptide of the present disclosure may be included in an amount of $10^3$ IU to $10^{12}$ IU (10 PFU to $10^{10}$ PFU) or $10^5$ IU to $10^{10}$ IU, but is not limited thereto.

Further, the cell including the polynucleotide encoding the peptide may be included in an amount of $10^3$ cells to $10^8$ cells, for example, $10^4$ cells to $10^8$ cells, $10^3$ cells to $10^7$ cells, or $10^4$ cells to $10^7$ cells.

With regard to the effective dose of the composition including the vector or cell including the polynucleotide encoding the peptide as an active ingredient, the vector may be administered in an amount of 0.05 mg/kg to 12.5 mg/kg, the recombinant virus may be administered in an amount of $10^7$ viral particles to $10^{11}$ viral particles ($10^5$ IU to $10^9$ IU)/kg, and the cell may be administered in an amount of $10^3$ cells/kg to $10^6$ cells/kg, or the vector may be administered in an amount of 0.1 mg/kg to 10 mg/kg, the recombinant virus may be administered in an amount of $10^8$ viral particles to $10^{10}$ viral particles ($10^6$ IU to $10^8$ IU)/kg, and the cell may be administered in an amount of $10^2$ cells/kg to $10^5$ cells/kg twice or three times a day. The composition is not particularly limited thereto, and may vary depending on a patient's conditions and development of the neurodegenerative disease.

The composition may further include a carrier, an excipient, and a diluent which are commonly used in the preparation of pharmaceutical compositions. The composition may be parenterally administered, and the parenteral administration may be selected from skin external application, intraperitoneal injection, intrarectal injection, subcutaneous injection, intravenous injection, intramuscular injection, and intrathoracic injection, but is not limited thereto.

The composition may be formulated in the form of an external preparation, a suppository, and a sterile injectable solution according to common methods, respectively. The carrier, the excipient, and the diluent which may be included in the composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil. The formulation may be prepared using a commonly used diluent or excipient, such as a filler, an extender, a binder, a wetting agent, a disintegrant, a surfactant, etc. A formulation for parenteral administration may include a sterilized aqueous solution, a non-aqueous solvent, a suspension, an emulsion, a lyophilized formulation, and a suppository. The non-aqueous solvent formulation and the suspension formulation may be propylene glycol, polyethylene glycol, a vegetable oil such as olive oil, or injectable ester such as ethyloleate. A base for the suppository formulation may be witepsol, macrogol, tween 61, cacao butter, laurin butter, glycerogelatin, etc.

Still another aspect provides a method of preventing or treating a neurodegenerative disease, the method including administering the composition including, as an active ingredient, the peptide, one or more polynucleotides encoding the peptide, the vector including the polynucleotide, or the host cell including the vector.

An appropriate administration dose of the composition may vary depending on a patient's conditions and body weight, severity of the disease, a type of a drug, administration route and period, but may be appropriately selected by those skilled in the art. For better effects, the composition may be administered at a dose of 0.0001 mg/kg to 1 g/kg or 0.001 mg/kg to 200 mg/kg per day, but is not limited thereto. The administration may be performed once or several times a day. However, the administration dose does not limit the scope of the present disclosure in any aspect. Further, the therapeutic agent may be administered via various routes to mammals such as rats, mice, livestock, humans, etc. All modes of administration are contemplated, for example, administration may be made orally, rectally, or by intravenous, intramuscular, subcutaneous, intradural, or intracerebroventricular injection.

Still another aspect provides use of the composition including, as an active ingredient, the peptide, one or more polynucleotides encoding the peptide, the vector including the polynucleotide, or the host cell including the vector in the preparation of a prophylactic or therapeutic agent for a neurodegenerative disease.

The peptide of the present disclosure may bind to EPOR and may inhibit cell death without the side effect of cell proliferation, thereby being usefully applied as an EPO substitute to the prevention or treatment of a neurodegenerative disease.

Advantageous Effects of Disclosure

A peptide according to an aspect has a simple structure, as compared with natural human erythropoietin, and thus the peptide easily passes through a tissue-blood barrier, exhibits excellent physiological activity due to cell protective effects, and is economically advantageous due to its low production cost. Further, the peptide has no side effect of cell proliferation, and thus a pharmaceutical composition including the erythropoietin-derived peptide of an aspect as an active ingredient may be usefully applied to the prevention or treatment of cell damage-related illnesses such as stroke, mechanical damage or ischemic injury to the nervous system, myocardial infarction, retinal damage, diabetes, etc., and the prevention of cell damages.

EXAMPLES

Hereinafter, exemplary embodiments will be provided for better understanding of the present disclosure. However, the following exemplary embodiments are provided only for understanding the present disclosure more easily, but the content of the present disclosure is not limited thereby.

Example 1. Synthesis of Erythropoietin-Derived Peptides

Erythropoietin-derived peptides of the present disclosure were synthesized as monomers according to a known solid phase peptide synthesis technology (Peptron, Daejeon, Korea).

In detail, erythropoietin-derived peptides which are able to bind to crucial amino acid sequences (Arg103, Ser104, Leu105, Leu108 and Arg110) in a sequence of a target site (site 2) of the natural erythropoietin receptor were synthesized, and specific characteristics of the peptides were examined, respectively. To determine concentrations of the synthesized peptides, liquid chromatography/mass selective detector (HP 1100 series) was used. Purity was measured by high performance liquid chromatography (SHIMADZU prominence HPLC) (>95% purity). The erythropoietin-derived peptides are shown in Table 1 below.

TABLE 1

| Peptide name | Sequence | SEQ ID NO: | Peptide name | Sequence | SEQ ID NO: |
|---|---|---|---|---|---|
| ML1 | LQLHVDKAVSGLRSLTTLLRALG | 1 | ML1-1 | LQLHVLKRVSGLLSHTMLLKALG | 9 |
| ML2 | LHVDKAVSGLRSLTTLLRAL | 2 | ML2-1 | RHVQKAESGLRSLTKLLREL | 10 |

TABLE 1-continued

| Peptide name | Sequence | SEQ ID NO: | Peptide name | Sequence | SEQ ID NO: |
|---|---|---|---|---|---|
| ML3 | TKVNFYAWKR | 3 | ML3-1 | TRVNYQAWKR | 11 |
| ML4 | DKAVSGLRSLTTLLRAL GAQKEAI | 4 | ML4-1 | KKAVSGLKTLTHILRALG AQKEAI | 12 |
| ML5 | SGLRSLTTLLRALG | 5 | ML5-1 | AGLRSRAHLRRALA | 13 |
| ML6 | SGLRSLTTLLRALGAQK EAI | 6 | ML6-1 | KGLRSLISLLRALGAQKE AI | 14 |
| ML7 | WEPLQLHVDKAVSGLR SLTTLLRAL | 7 | ML7-1 | DEALDLEVDKAATGLRT LTTLIRAL | 15 |
| ML8 | DKAVSGLRSLTTLLRAL | 8 | ML8-1 | NKAVAGLRSLTVN | 16 |

Hydrophobicity, charge, and isoelectric point (pI) of the erythropoietin-derived peptides, ML1-1, ML2-1, ML3-1, ML4-1, ML5-1, ML6-1, ML7-1, and ML8-1 were calculated and shown in Table 2 below.

TABLE 2

| Peptide name | Hydrophobicity | Charge (pH 7) | pI | Target site |
|---|---|---|---|---|
| ML1-1 | 8.25 | 3.4 | 11.2 | 2 |
| ML2-1 | -4.45 | 3.2 | 10.94 | 2 |
| ML3-1 | -10.07 | 2.9 | 10.94 | 1 |
| ML4-1 | 5 | 6.1 | 11.41 | 2 |
| ML5-1 | -4.15 | 4.1 | 12.48 | 2 |
| ML6-1 | 8.85 | 2.9 | 10.94 | 2 |
| ML7-1 | 2.05 | -2.1 | 4.59 | 2 |
| ML8-1 | 5.7 | 1.9 | 11.12 | 2 |

TABLE 3

| Peptide name | Sequence | SEQ ID NO: |
|---|---|---|
| ML1 | LQLHVDKAVSGLRSLTTLLRALG | 1 |
| ML1-H1 | LQLHVLKAVSGLLTHTTLLKALG | 17 |
| ML1-H2 | LQLHVLKAVSGLLTLTMIRRALG | 18 |
| ML1-H3 | LQLHVLKAVAGLRTLAMIRRALA | 19 |

TABLE 4

| Peptide name | Number of residue | Molecular weight | Absorption coefficient | Isoelectric point | Net charge (pH 7) | Predicted solubility |
|---|---|---|---|---|---|---|
| ML.1 | 23 | 2461.9 g/mol | 0 $M^{-1}cm^{-1}$ | pH 11.23 | 2.1 | Low solubility in water |
| ML1-H1 | 23 | 2426.94 g/mol | 0 $M^{-1}cm^{-1}$ | pH 10.73 | 2.2 | Low solubility in water |
| ML1-H2 | 23 | 2504.09 g/mol | 0 $M^{-1}cm^{-1}$ | pH 12.13 | 3.1 | Low solubility in water |
| ML1-H3 | 23 | 2515.12 g/mol | 0 $M^{-1}cm^{-1}$ | pH 12.41 | 4.1 | Low solubility in water |

Example 2. Synthesis of Erythropoietin-Derived Peptides Using Partial Sequence (1)

For sequence modification experiments, a binding model of erythropoietin and its receptor was based on a previously known binding structure (Protein Data Bank ID: 1EER). Based on known characteristics of amino acids, amino acids of the erythropoietin-derived peptides were substituted. Amino acids are classified into 4 types (1) non-polar or hydrophobic, 2 neutral, 3 negatively charged, 4 positively charged) according to polarity of their side chains. Based on information of non-polar (hydrophobic), neutral, negatively charged, or positively charged amino acids, the existing amino acid sequences were substituted to induce modification in respective characteristics.

Peptides prepared by partially modifying sequences of ML1 peptide and their characteristics are shown in Tables 3 and 4.

Example 3. Synthesis of Erythropoietin-Derived Peptides Using Partial Sequence (2)

Partial sequences of the peptides were substituted using the basic sequence of ML1 as in Example 2. In this regard, amino acids were substituted based on the existing binding model of erythropoietin and its receptor without hindering the existing binding structure (a distance between proteins or a protein structure). FIG. 7 illustrates exemplary substitution of amino acid sequences. Since substitution of alanine (Ala) with arginine (Arg) hinders the existing binding, substitution with serine (Ser) may be performed to prevent hindrance of the binding.

Peptides prepared by modifying the charge of the ML1 peptide and characteristics thereof are shown in Tables 5 and 6 below.

TABLE 5

| Peptide name | Sequence | SEQ ID NO: |
|---|---|---|
| ML1-C1 | LDLEVDKAVSGLRSLTTLLRALG | 20 |
| ML1 | LQLHVDKAVSGLRSLTTLLRALG | 1 |
| ML1-C2 | LQRHVDKRVSGLRSLTTLLRALG | 21 |
| ML1-C3 | LQRHVKKRVKGLKSLTTLLRALG | 22 |

TABLE 6

| Peptide name | Number of residue | Molecular weight | Absorption coefficient | Isoelectric point | Net charge (pH 7) | Predicted solubility |
|---|---|---|---|---|---|---|
| ML1-C1 | 23 | 2440.83 g/mol | 0 $M^{-1}cm^{-1}$ | pH 6.96 | 0 | High solubility in water |
| ML1 | 23 | 2461.9 g/mol | 0 $M^{-1}cm^{-1}$ | pH 11.23 | 2.1 | Low solubility in water |
| ML1-C2 | 23 | 2590.04 g/mol | 0 $M^{-1}cm^{-1}$ | pH 12.12 | 4.1 | High solubility in water |
| ML1-C3 | 23 | 2616.21 g/mol | 0 $M^{-1}cm^{-1}$ | pH 12.45 | 7.1 | High solubility in water |

Example 4. Synthesis of Erythropoietin-Derived Peptides Using Partial Sequence (3)

A partial sequence "LHVDKAVSGLRSLTTL" of the ML1 basic sequence was used to prepare peptides having modified amino acids at both ends thereof, as in Table 7 below.

TABLE 7

| Peptide name | Sequence | SEQ ID NO: |
|---|---|---|
| ML1-L2 | L HVDKAVSGLRSLTT L | 23 |
| ML1-K2 | K HVDKAVSGLRSLTT K | 24 |
| ML1-R2 | R HVDKAVSGLRSLTT R | 25 |

Experimental Example

I. Determination of Binding Affinity of Erythropoietin-Derived Peptide to Erythropoietin Receptor (EPOR)

To determine whether the erythropoietin-derived peptides prepared in Examples 1 to 3 are able to bind to the erythropoietin receptor having the target site to exert their actions, a surface plasmon resonance (SPR) technique was used to determine binding affinity. The SPR technique is to measure interactions between biomolecules in real-time by using an optical principle without specific labeling, and is a system analyzing affinity between two molecules and kinetics, i.e., an association rate (Ka) and a dissociation rate (Kd).

In detail, real-time SPR analysis may be performed using Reichert® SPR Biosensor SR 7500C instrument (Reichert® Inc., NY, USA). Soluble mouse EPOR chimera proteins (R&D Systems™, Minneapolis, MN, USA) were covalently linked to a carboxymethylated dextran matrix-coated chip (BR-1005-39, Pharmacia Biosensor AB) by an amine coupling procedure using an amine coupling kit (BR-1000-50, GE Healthcare, USA) in accordance with manufacturer's instructions. Each 5 µM, 2.5 µM, and 1.25 µM of the peptide samples of the present disclosure and scrambled peptides were applied at a flow rate of 5 µl/minute, and the experiments were independently performed in duplicate. For signal normalization, DMSO was applied at a flow rate of 5 µl/minute. After each binding cycle, the sensor chip was regenerated by injecting 25 mM of acetic acid at a flow rate of 20 µl/minute.

As a result, as shown in FIG. 1, the result values were increased according to the concentrations of the erythropoietin-derived peptides of one embodiment, and thus it was confirmed that the erythropoietin-derived peptides bind to the erythropoietin receptor having the target site to exert their actions (FIG. 1). Further, as shown in Tables 8 and 9, it was also confirmed that the erythropoietin-derived peptides of one embodiment exhibited binding affinities similar to the known binding affinity (~1 µM).

TABLE 8

| | Ka | Kd | KD |
|---|---|---|---|
| ML1 | $1.311 \times 10^3$ | $8.5 \times 10^{-3}$ | 6.46077 µM |
| ML2 | $1.6 \times 10$ | $4.4 \times 10^{-3}$ | 273 µM |
| ML3 | $2.05 \times 10^2$ | $3 \times 10^{-3}$ | 14.6341 µM |
| ML4 | $2.2 \times 10^2$ | $2.2 \times 10^{-3}$ | 10 µM |
| ML5 | $3.04 \times 10^2$ | $0.1 \times 10^{-3}$ | 0.32894 µM |
| ML6 | $5.0 \times 10$ | $4.5 \times 10^{-2}$ | 900 µM |
| ML7 | $3.00 \times 10^2$ | $0.2 \times 10^{-2}$ | 6.666 µM |
| ML8 | $1.8 \times 10^2$ | $0.8 \times 10^{-1}$ | 444.44 µM |
| ML1-1 | $5.55 \times 10^3$ | $5.9 \times 10^{-3}$ | 1.06 µM |
| ML2-1 | $3.1 \times 10^2$ | $4.1 \times 10^{-3}$ | 14.3 µM |
| ML3-1 | $3.08 \times 10^3$ | $1.3 \times 10^{-2}$ | 4.31 µM |
| ML4-1 | $4.10 \times 10^2$ | $1.20 \times 10^2$ | 39.34 mM |
| ML5-1 | $4.42 \times 10^2$ | $3.46 \times 10^{-2}$ | 78.28 µM |
| ML6-1 | $1.9 \times 10^2$ | $3 \times 10^{-2}$ | 157.8 µM |
| ML7-1 | $2.26 \times 10^2$ | $1.44 \times 10^{-2}$ | 63.70 µM |
| ML8-1 | $6.4 \times 10$ | $1.5 \times 10^{-1}$ | 2.37 mM |

TABLE 9

| | Km | Ka | Kd | KD |
|---|---|---|---|---|
| ML1 | 1.26E+05 | 1310.8 | 8.47E−03 | 6.46077 µM |
| ML1-H1 | 4.79E+05 | 1.01E+03 | 7.94E−03 | 7.84542 µM |
| ML1-H2 | 1.00E+10 | 3434.3 | 1.05E−03 | 306.977 nM |
| ML1-H3 | 1.00E+10 | 4157.6 | 4.77E−03 | 1.14651 µM |
| ML1-C1 | 9.23E+05 | 1745.7 | 0.2617 | 149.921 µM |
| ML1-C2 | 4.58E+05 | 1.59E+03 | 0.01876 | 11.7609 µM |
| ML1-C3 | 1.46E+05 | 1104.9 | 0.01086 | 9.82836 µM |

In other words, it was confirmed that the peptides according to specific embodiments are those derived from the erythropoietin binding site, and thus they have binding affinity to the erythropoietin receptor.

Determination of Secondary Alpha-Helix Formation of Erythropoietin-Derived Peptide The present inventors determined whether the erythropoietin-derived peptides synthesized in Example 1 are able to form a stable alpha-helix, like natural erythropoietin.

As a result, it was confirmed that the erythropoietin-derived peptides synthesized in Example 1 formed a stable secondary alpha-helix, like natural erythropoietin.

II. Determination of Cell Protective Effect of Erythropoietin-Derived Peptide (1)

To determine whether the erythropoietin-derived peptides prepared in Examples 1 to 3 exhibit cell protective effects, cell viability was determined under stress conditions where an increase in reactive oxygen species was induced by hydrogen peroxide ($H_2O_2$).

In detail, to evaluate cell viability, an MTS assay (Cell-Titer 96® Aqueous One Solution Cell Proliferation Assay, Promega, Madison, WI, USA) was performed. PC12 cells were seeded in a 96-well plate ($5 \times 10^4$ cells per well), and an increase in reactive oxygen species was induced using 150 UM of hydrogen peroxide ($H_2O_2$). Thereafter, 25 ng/ml of nerve growth factor (NGF) was added as a positive control group, and 1 IU/ml of the erythropoietin compound, 0.25 pM, 1 pM, 2 pM, or 4 pM of the peptide of Example 1, each 0.25 pM, 1 pM, 2 pM, 10 pM, or 100 pM of the peptides of Example 2 and 3, or 0.1 pM, 1 pM, 50 pM, or 0.5 nM of the peptide of Example 4 was added, and 20 µl of an MTS solution was added to each well, and left for 3 hours. The initial number of cells (0 hour) and the number of cells after 48 hours were counted. Intracellular soluble formazan produced by cell reduction was determined by recording absorbance of each 96-well plate at a wavelength of 490 nm using a VERSA MAX.

As a result, as shown in FIG. 2, it was confirmed that the erythropoietin-derived peptides protected cells from cell death caused by the increase in reactive oxygen species (FIG. 2). This result was similar to the cell protective effect by treatment with the natural erythropoietin compound.

III. Determination of Cell Protective Effect of Erythropoietin-Derived Peptide (2)

To determine whether the erythropoietin-derived peptide prepared in Example 4 exhibits the cell protective effect, mitochondrial activity was determined under stress conditions where an increase in reactive oxygen species was induced by hydrogen peroxide ($H_2O_2$).

In detail, PC12 cells or human SH-SY5Y cells were seeded in a 96-well plate ($5 \times 10^4$ cells per well), and an increase in reactive oxygen species was induced using 150 µM of hydrogen peroxide ($H_2O_2$). Thereafter, 25 ng/ml of NGF was added as a positive control group, 1 IU/ml of the erythropoietin compound, or 0.1 pM, 1 pM, 50 pM, or 0.5 nM of the peptide of Example 4 were added.

When mitochondrial activity is suppressed, mitochondrial swelling due to abnormalities of the mitochondrial membrane potential, dysfunction due to oxidative stress such as reactive oxygen species or free radicals, dysfunction due to genetic factors, and dysfunction due to defects in oxidative phosphorylation for mitochondrial energy production occur. Thus, mitochondrial activity may be determined by measuring the mitochondrial membrane potential. Tetramethylrhodamine methyl ester (TMRM) staining of mitochondria was performed. Since TMRM staining intensity is increased in proportion to the mitochondrial membrane potential, the intracellular mitochondrial membrane potential was determined by measuring the TMRM staining intensity using a microplate reader (excitation, 485 nm; emission, 535 nm).

As a result, as shown in FIG. 3, it was confirmed that the erythropoietin-derived peptides suppressed inhibition of mitochondrial activity caused by increased reactive oxygen species (FIG. 3). This result was similar to the effect by treatment with the natural erythropoietin compound.

IV. Determination of Cell Proliferation-Inhibitory Effect of Erythropoietin-Derived Peptide (1)

Side effects such as cell proliferation were determined for the three peptides (ML1-L2, ML1-K2, and ML1-R2) prepared in Example 4.

In detail, to determine cell proliferation degree, an MTS assay (CellTiter 96® Aqueous One Solution Cell Proliferation Assay, Promega, Madison, WI, USA) was performed. PC12 cells were seeded in a 96-well plate ($5 \times 10^4$ cells per well), and 1 pM of scrambled peptide (Scr) as a negative control group, 0.5 IU/ml, 1 IU/ml, or 10 IU/ml of the erythropoietin compound, or 1 pM, 10 pM, or 0.5 nM of the peptide of Example 4 was added, and 20 µl of an MTS solution was added to each well, and left for 3 hours. The initial number of cells (0 hour) and the number of cells after 48 hours were counted. Intracellular soluble formazan produced by cell reduction was determined by recording absorbance of each 96-well plate at a wavelength of 490 nm using a VERSA MAX.

As a result, as shown in FIG. 4, it was confirmed that all the peptides showed cell proliferation rates similar to that of the control group, and they showed no side effect of cell proliferation.

V. Determination of Cell Proliferation-Inhibitory Effect of Erythropoietin-Derived Peptide (2)

To determine the side effect of cell proliferation with respect to the peptides prepared in Examples 1 to 3, cell viability was evaluated by an MTT assay.

In detail, PC12 cells were cultured in a DMEM (Dulbecco's Modified Eagle's Medium) medium (Hyclone™, USA) and an RPMI1640 medium (Hyclone™, UT, USA) each supplemented with 10% fetal bovine serum (FBS, Hyclone™, UT, USA), 100 unit/ml penicillin, and 100 µg/ml streptomycin (Hyclone™, UT, USA) in an incubator under conditions of 5% $CO_2$ and 37° C. PC12 cells were seeded in a 96-well culture plate at a density of $5 \times 10^4$ cells/ml, and cultured under conditions of 37° C. and 5% $CO_2$ for 24 hours. Thereafter, the cells were treated with each of the peptides of Examples 1 to 3 which were prepared at a concentration of 10 ng/ml, followed by incubation for 24 hours. Thereafter, 20 µl of 5 mg/ml 3-[4,5-dimethyl-thiazol]-2,5-diphenyl-tetrazolium bromide (MTT) reagent was added thereto, and allowed to react for 2 hours. After reaction, 200 µl of dimethyl sulfoxide (DMSO, Duksan, Gyeonggi-do, Korea) was added thereto to completely dissolve formed formazan, and absorbance at 570 nm was measured using a microplate reader (Molecular Devices, CA, USA).

As a result, as shown in FIG. 5, it was confirmed that all the peptides showed cell proliferation rates similar to that of the control group, and they showed no side effect of cell proliferation.

The foregoing description of the present disclosure is for illustrative purposes only, and those of ordinary skill in the art readily understand that the present disclosure may be implemented in a different specific form without changing the technical spirit or essential characteristics thereof. It is therefore to be understood that the above-described embodiments are not limitative, but illustrative in all aspects.

The invention claimed is:

1. A peptide comprising the amino acid sequence of SEQ ID NO: 18.

2. The peptide of claim 1, wherein the peptide binds to an erythropoietin receptor.

3. The peptide of claim 1, wherein the peptide forms an alpha-helical structure.

4. The peptide of claim 1, wherein the peptide exhibits cell protective activity against oxidative damage induced by reactive oxygen species or $H_2O_2$.

5. The peptide of claim 1, wherein the peptide has no side effect of cell proliferation induced by binding of a natural erythropoietin to the erythropoietin receptor.

6. A pharmaceutical composition comprising the peptide of claim 1.

7. A method for protecting cells from oxidative damage induced by reactive oxygen species, comprising:
   i) culturing and treating the cells with $H_2O_2$;
   ii) administering the composition of claim 6 to the cells of step i) in vitro, thereby protecting the cells of step i) from oxidative damage induced by increased reactive oxygen species due to $H_2O_2$, wherein the protection of the cells against the oxidative damage is determined by detecting suppression of inhibition of mitochondrial activity caused by increased reactive oxygen species induced by H2O2 in the cells of step ii) as compared to the cells of step i).

* * * * *

SEQUENCE LISTING

```
Sequence total quantity: 25
SEQ ID NO: 1            moltype = AA  length = 23
FEATURE                 Location/Qualifiers
REGION                  1..23
                        note = peptide ML1
source                  1..23
                        mol_type = protein
                        organism = synthetic construct
SEQUENCE: 1
LQLHVDKAVS GLRSLTTLLR ALG                                                   23

SEQ ID NO: 2            moltype = AA  length = 20
FEATURE                 Location/Qualifiers
REGION                  1..20
                        note = peptide ML2
source                  1..20
                        mol_type = protein
                        organism = synthetic construct
SEQUENCE: 2
LHVDKAVSGL RSLTTLLRAL                                                       20

SEQ ID NO: 3            moltype = AA  length = 10
FEATURE                 Location/Qualifiers
REGION                  1..10
                        note = peptide ML3
source                  1..10
                        mol_type = protein
                        organism = synthetic construct
SEQUENCE: 3
TKVNFYAWKR                                                                  10

SEQ ID NO: 4            moltype = AA  length = 24
FEATURE                 Location/Qualifiers
REGION                  1..24
                        note = peptide ML4
source                  1..24
                        mol_type = protein
                        organism = synthetic construct
SEQUENCE: 4
DKAVSGLRSL TTLLRALGAQ KEAI                                                  24

SEQ ID NO: 5            moltype = AA  length = 14
FEATURE                 Location/Qualifiers
REGION                  1..14
                        note = peptide ML5
source                  1..14
                        mol_type = protein
                        organism = synthetic construct
SEQUENCE: 5
SGLRSLTTLL RALG                                                             14

SEQ ID NO: 6            moltype = AA  length = 20
FEATURE                 Location/Qualifiers
REGION                  1..20
                        note = peptide ML6
source                  1..20
                        mol_type = protein
                        organism = synthetic construct
SEQUENCE: 6
SGLRSLTTLL RALGAQKEAI                                                       20

SEQ ID NO: 7            moltype = AA  length = 25
FEATURE                 Location/Qualifiers
REGION                  1..25
                        note = peptide ML7
source                  1..25
                        mol_type = protein
                        organism = synthetic construct
SEQUENCE: 7
WEPLQLHVDK AVSGLRSLTT LLRAL                                                 25

SEQ ID NO: 8            moltype = AA  length = 17
FEATURE                 Location/Qualifiers
REGION                  1..17
                        note = peptide ML8
source                  1..17
                        mol_type = protein
                        organism = synthetic construct
```

```
SEQUENCE: 8
DKAVSGLRSL TTLLRAL                                                          17

SEQ ID NO: 9           moltype = AA  length = 23
FEATURE                Location/Qualifiers
REGION                 1..23
                       note = peptide ML1-1
source                 1..23
                       mol_type = protein
                       organism = synthetic construct
SEQUENCE: 9
LQLHVLKRVS GLLSHTMLLK ALG                                                   23

SEQ ID NO: 10          moltype = AA  length = 20
FEATURE                Location/Qualifiers
REGION                 1..20
                       note = peptide ML2-1
source                 1..20
                       mol_type = protein
                       organism = synthetic construct
SEQUENCE: 10
RHVQKAESGL RSLTKLLREL                                                       20

SEQ ID NO: 11          moltype = AA  length = 10
FEATURE                Location/Qualifiers
REGION                 1..10
                       note = peptide ML3-1
source                 1..10
                       mol_type = protein
                       organism = synthetic construct
SEQUENCE: 11
TRVNYQAWKR                                                                  10

SEQ ID NO: 12          moltype = AA  length = 24
FEATURE                Location/Qualifiers
REGION                 1..24
                       note = peptide ML4-1
source                 1..24
                       mol_type = protein
                       organism = synthetic construct
SEQUENCE: 12
KKAVSGLKTL THILRALGAQ KEAI                                                  24

SEQ ID NO: 13          moltype = AA  length = 14
FEATURE                Location/Qualifiers
REGION                 1..14
                       note = peptide ML5-1
source                 1..14
                       mol_type = protein
                       organism = synthetic construct
SEQUENCE: 13
AGLRSRAHLR RALA                                                             14

SEQ ID NO: 14          moltype = AA  length = 20
FEATURE                Location/Qualifiers
REGION                 1..20
                       note = peptide ML6-1
source                 1..20
                       mol_type = protein
                       organism = synthetic construct
SEQUENCE: 14
KGLRSLISLL RALGAQKEAI                                                       20

SEQ ID NO: 15          moltype = AA  length = 25
FEATURE                Location/Qualifiers
REGION                 1..25
                       note = peptide ML7-1
source                 1..25
                       mol_type = protein
                       organism = synthetic construct
SEQUENCE: 15
DEALDLEVDK AATGLRTLTT LIRAL                                                 25

SEQ ID NO: 16          moltype = AA  length = 13
FEATURE                Location/Qualifiers
REGION                 1..13
                       note = peptide ML8-1
source                 1..13
                       mol_type = protein
```

```
                        organism = synthetic construct
SEQUENCE: 16
NKAVAGLRSL TVN                                                      13

SEQ ID NO: 17           moltype = AA   length = 23
FEATURE                 Location/Qualifiers
REGION                  1..23
                        note = peptide ML1-H1
source                  1..23
                        mol_type = protein
                        organism = synthetic construct
SEQUENCE: 17
LQLHVLKAVS GLLTHTTLLK ALG                                           23

SEQ ID NO: 18           moltype = AA   length = 23
FEATURE                 Location/Qualifiers
REGION                  1..23
                        note = peptide ML1-H2
source                  1..23
                        mol_type = protein
                        organism = synthetic construct
SEQUENCE: 18
LQLHVLKAVS GLLTLTMIRR ALG                                           23

SEQ ID NO: 19           moltype = AA   length = 23
FEATURE                 Location/Qualifiers
REGION                  1..23
                        note = peptide ML1-H3
source                  1..23
                        mol_type = protein
                        organism = synthetic construct
SEQUENCE: 19
LQLHVLKAVA GLRTLAMIRR ALA                                           23

SEQ ID NO: 20           moltype = AA   length = 23
FEATURE                 Location/Qualifiers
REGION                  1..23
                        note = peptide ML1-C1
source                  1..23
                        mol_type = protein
                        organism = synthetic construct
SEQUENCE: 20
LDLEVDKAVS GLRSLTTLLR ALG                                           23

SEQ ID NO: 21           moltype = AA   length = 23
FEATURE                 Location/Qualifiers
REGION                  1..23
                        note = peptide ML1-C2
source                  1..23
                        mol_type = protein
                        organism = synthetic construct
SEQUENCE: 21
LQRHVDKRVS GLRSLTTLLR ALG                                           23

SEQ ID NO: 22           moltype = AA   length = 23
FEATURE                 Location/Qualifiers
REGION                  1..23
                        note = peptide ML1-C3
source                  1..23
                        mol_type = protein
                        organism = synthetic construct
SEQUENCE: 22
LQRHVKKRVK GLKSLTTLLR ALG                                           23

SEQ ID NO: 23           moltype = AA   length = 16
FEATURE                 Location/Qualifiers
REGION                  1..16
                        note = peptide ML1-L2
source                  1..16
                        mol_type = protein
                        organism = synthetic construct
SEQUENCE: 23
LHVDKAVSGL RSLTTL                                                   16

SEQ ID NO: 24           moltype = AA   length = 16
FEATURE                 Location/Qualifiers
REGION                  1..16
                        note = peptide ML1-K2
source                  1..16
```

```
                    mol_type = protein
                    organism = synthetic construct
SEQUENCE: 24
KHVDKAVSGL RSLTTK                                              16

SEQ ID NO: 25       moltype = AA   length = 16
FEATURE             Location/Qualifiers
REGION              1..16
                    note = peptide ML1-R2
source              1..16
                    mol_type = protein
                    organism = synthetic construct
SEQUENCE: 25
RHVDKAVSGL RSLTTR                                              16
```